United States Patent [19]

Landwehr

[11] Patent Number: 4,845,518
[45] Date of Patent: Jul. 4, 1989

[54] PHOTOGRAPHICALLY MEASURING SURFACE CONTOURS AND DIMENSIONS

[76] Inventor: Ulrich M. Landwehr, Bahnhofstrasse 8, D-3000 Hannover 1, Fed. Rep. of Germany

[21] Appl. No.: 109,080

[22] Filed: Oct. 16, 1987

[30] Foreign Application Priority Data

Sep. 24, 1986 [DE] Fed. Rep. of Germany ....... 3632450

[51] Int. Cl.⁴ .............................................. G03B 29/00
[52] U.S. Cl. ..................................................... 354/77
[58] Field of Search ........................... 354/77, 106–109

[56] References Cited

U.S. PATENT DOCUMENTS

| | | | |
|---|---|---|---|
| 3,169,459 | 2/1965 | Friedberg et al. | 354/77 X |
| 3,376,800 | 4/1968 | Faasch | 354/77 |
| 3,610,120 | 10/1971 | Morse et al. | 354/109 |
| 3,919,474 | 11/1975 | Benson | 355/52 X |
| 4,533,224 | 8/1985 | Ou | 354/77 |
| 4,639,107 | 1/1987 | Landwehr | 354/77 |

Primary Examiner—Donald A. Griffin
Attorney, Agent, or Firm—Ralf H. Siegemund

[57] ABSTRACT

An apparatus for ascertaining size and topographic measurements of a person by means of photography whereby a measuring raster is to be superimposed on an image when used by a photographic or video camera; the apparatus is improved by means of a slide raster inside the camera.

7 Claims, 2 Drawing Sheets

PHOTOGRAPHICALLY MEASURING SURFACE CONTOURS AND DIMENSIONS

BACKGROUND OF THE INVENTION

The present invention relates to the acquisition of data representing topographic and pictorial representations of dimensions of an object, by means of photography; and more particularly the invention relates to the photographic acquisition of data representing size and related measurements of the body of a human being whereby specifically photographic image is provided of the object of interest such as the body of a person in conjunction and under superpositioning with a measuring raster.

German printed patent application 34 25 913 corresponding to U.S. Pat. No. 4,639,107 and Canadian patent application, SN 485,303, filed June 26, 1985, which discloses during the taking of a picture of a person, horizontal lines are projected at an oblique angle from above on the person to be photographed while on the other hand and independently therefrom a measuring raster is concurrently projected into the plane of imaging and/or photography without such oblique distortion. The raster as per this patent is laterally inserted into the main imaging path through a semi-transparent mirror which is placed at an angle in front of the objective of the camera (FIG. 1, 2 of that patent). In a particular embodiment shown the measuring raster is introduced by means of the mirror whereby the distance between a wall having the measuring raster from the mirror is exactly or at least approximately similar to the spacing of the object to the photographed from that mirror. This procedure has a disadvantage that relatively large space and areas are required.

In accordance with another embodiment (FIG. 3) of that patent the measuring raster is projected by means of a flash projector using a slide which carries the raster at a much smaller scale. Still this procedure requires relatively large space. That disadvantage can be reduced as to its effectiveness in that one uses an objective lens having a very large depth of field. However, such lenses are usually quite expensive.

The two approaches are further disadvantaged by the fact that it requires high degree of adjustment accuracy. In the case of carelessness on the part of an operating person this accuracy may easily be eliminated so that incorrect measurements are taken and deduced from the photograph. Still, the U.S. Pat. No. 4,639,107 was as such a significant development and improvement from an earilier version, that is U.S. Pat. No. 4,370,039.

DESCRIPTION OF THE INVENTION

It is an object of the present invention to provide a new and improved device of the kind mentioned above which, however, can be used and practiced in relatively small rooms and spaces, i.e. the demands for larger spaces can be dropped; in addition there should be a lack of sensitivity and criticality as to adjustment and no sensitivity to undesired light from parasitic sources.

In accordance with the preferred embodiment of the present invention a slide projector is provided inside the camera i.e. the camera as such is reconstructed to obtain a dual function, namely, projecting the measuring raster (vertical and horizontal lines) into the imaging plane and providing regular photography of the object (person) upon which (whom) that raster is now internally superimposed; the camera objective is bypassed in this approach.

It is apparent that a very compact design obtains through this kind of construction which is insensitive against undesired maladjustments since there is a limited accessibility. Also, the incorporation of the slide projection into the camera as such prevents undesired parasitic light from interfering with the projection of the measuring raster owing to bypassing the objective lens.

In furtherance of practicing the invention in a particular manner, it is suggested to provide a semi-transparent mirror inside a camera with an angle of about 45 degrees in relation to the imaging and film plane. This mirror is of course disposed between the objective of the camera and that film plane. The slide projector positioned inside the camera is oriented to that mirror so that the enlarged measuring raster is projected into the imaging ray path but without causing light from the object (person) and reaching the camera to be reflected.

Of particular advantage is to fasten the slide projector on the upper inside surface of the camera housing proper and the mirror is arranged at an angle of 45 degrees to the vertical. On the other hand and in principal the projector could be attached to the side wall on the inside of the camera with a corresponding 45 degrees inclination around the vertical axis.

In principle, one can omit the mirror inside the camera if the slide projector with the slide is in fact disposed on the inside front wall of the camera and the image of the raster is directly projected, at an angle to the optical axis, onto the imaging and film plane. In this case a high degree of accuracy as far as obtaining measurements are concerned requires the use of a correspondingly corrected or distorted raster on the slide in order to result in equidistant (or other predetermined) spacing of the measuring raster lines as projected onto and into the plane of the film. In the case of a projection slightly from above inside the camera i.e. the projector being disposed directly above the objective lens on the front wall of the housing it is required that the spacing of the horizontal lines in the slide is slightly decreased in down direction in order to result in equidistant spacing of the lines as projected. In principle, one could provide a direct projection from a side wall or from the side of the frame inside wall next to the objective. In this case, the vertical raster lines will be unequally spaced.

In order to adjust initially the projector inside the camera it is of advantage if, on positioniong the camera in relation to an object or to the plane in which the object is going to be placed, a vertical ruler be provided having appropriate markings and the projector of the measuring raster including the slide therein are then positioned oriented in relation to that ruler. Specifically then and in lieu of a film in the imaging plane one will place a ground or frosted glass plate. Since on ascertaining the dimensions of a human body the relationship of height to width is quite large; it is of advantage to use the film material twice and to shift the film in relation i.e. on taking the picture laterally over the first half and the second half separately in the case the film material has dimensions 7×10 cm and each image has dimensions of 3.5×10 cm then it is practical to provide on one half the front and the other half the side view of the object, i.e. of the person.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 is a schematic side view of a system arrangement generally of the type outlined above and specifically incorporating the features of the invention. Herein reference numeral 1 is a camera, specifically a camera housing improved in accordance with the inventive features i.e. it holds certain normally provided features as they are customary for a camera. It should be mentioned that the camera may be constructed to be of the instant type so that a picture is immediately produced and becomes available to the user for inspection and evaluation. A flashlight projector 2 is disposed above the camera 1 for projecting a line raster with horizontal lines during the taking of pictures upon the object to be photographed, 3. A flash projector of this kind is described in greater detail in German patent 29 48 010 corresponding to U.S. Pat. No. 4,370,039 corresponding to Canadian Pat. No. 1,155,651. The line raster projector 2 is provided to establish a line pattern on the object (or person) such that the resulting distortion of equidistantly spaced lines as projected onto an uneven surface is an indication of the surface's topography. This is also described in my U.S. Pat. Nos. 4,370,039 and 4,639,107.

Figure 1:
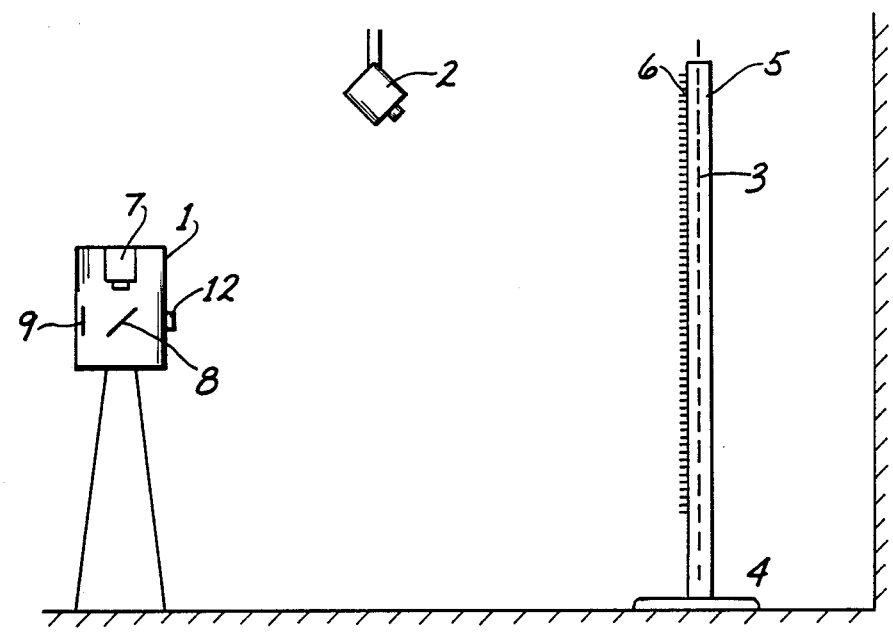
FIG. 1 is a somewhat schematic side elevation of a system and arrangement that employs features in accordance with the preferred embodiment of the present invention for practicing the best mode thereof.

Reference numeral 4 refers to a balancing plate which upon replacing the object 3 by human being assures a normal or standardized position and posture of that person during the taking of the picture. Such a balancing plate is shown for example in German printed patent application 33 01 864 but does not constitute a portion of the invention. A ruler 5 is disposed next to the object 3. The ruler is provided with markings 6 such as a plurality of equidistantly spaced markings which are provided for purposes of initial adjustment of the arrangement. This ruler is used for such adjustment while no films are placed in the camera but a frosted or ground glass plate in inserted instead for purposes of direct viaual observation.

In order to project a measuring raster upon the photograph a projector 7 is provided on the inside of the camera housing 1. Details of this projector and various examples would be described more fully below. Presently it suffices that for example a mirror 8 inside camera housing 1 is disposed into light path of projector 7 so that a slide is projected onto the film 9 or an adjusting plate for purposes of appropriate image superpositioning. Mirror 8 is semitransparent so that the object 3 can be still projected through the mirror 8 with very little light attenuation. Mirror 8 is realized e.g. through a glass plate upon which a very thin mercury layer has been vapor deposited.

Figure 2:
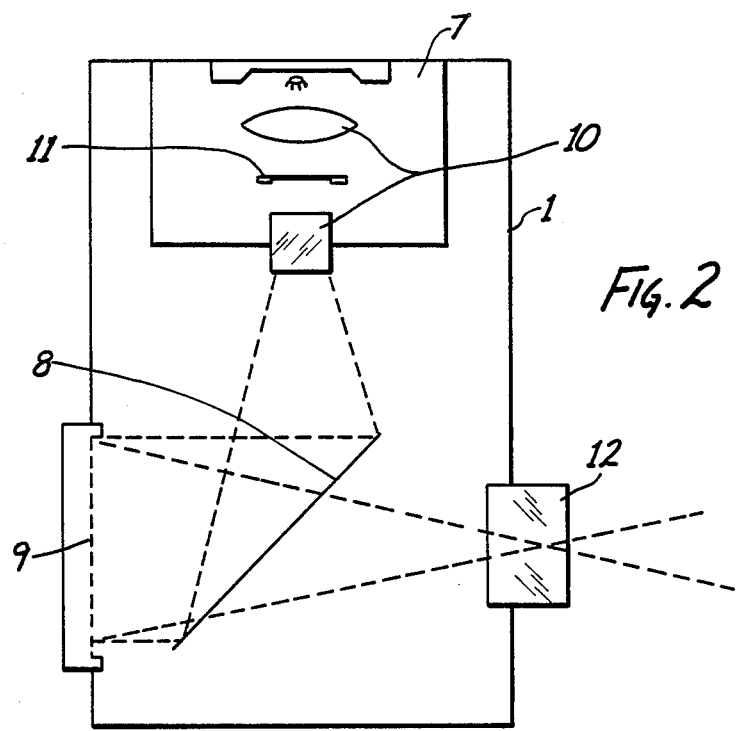
FIG. 2 is an inside view of a camera used for practicing the invention in the system and arrangement shown in FIG. 1.

FIG. 2 shows in detail an example for the camera 1 and on enlarged scale. The projector 7 includes an optical system 10 into which a slide 11 can be inserted carrying the raster to be projected. The measuring raster may be comprised of horizontal and vertical transparent lines carved on and into an opaque glass plate. The horizontal and vertical lines of the raster are preferably equidistantly spaced. The projected image of the raster is intercepted by the mirror 8 and projected onto film 9. Camera objective 12 images the object 3 (FIG. 1) onto the film 9.

Figure 3:
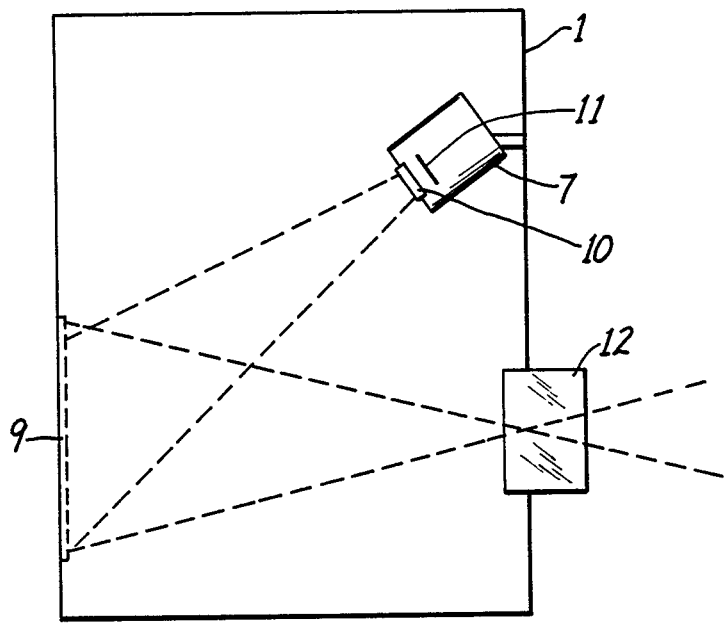
FIG. 3 and 4 are modifications of a camera construction.

The example shown in FIG. 3 deviates from the camera construction shown in FIG. 2 in that the projector 7 is not attached to the top of the camera - that is incidental. The principal aspect of FIG. 3 is to provide for a raster projection inside of the camera without the use of a mirror. Hence the projector 7 is disposed above the objective lens 12 i.e. it is attached to the front wall 1' of the camera housing 1. One can also say that FIG. 3 shows a projector system as well as the objective system 12 with a common plane established by the optical axes of each of them and without any interception provided for by any mirror or the like. In this case the projection provided by the projector 7 and there particularly the objective lens of the projector distorts the image so that the vertical spacing of the horizontal raster lines deviates from the spacing and the slide. Spacing on the slide is made nonlinear and equidistant spacing can be obtained as far as the projected horizontal raster lines are concerned.

Figure 4:
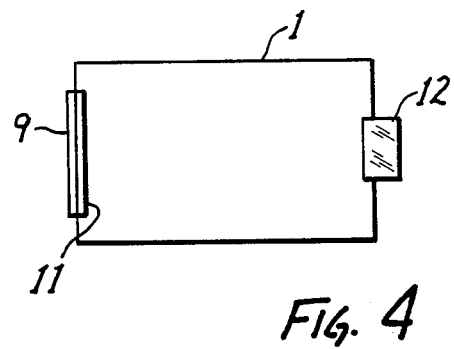

FIG. 4 illustrates another configuration of practicing the invention showing that in cases the projector as such can be dispensed with. In this case the raster slide 11 is arranged directly in front of the film 9 and it is slidable in horizontal and/or vertical direction. The film material 9 is used twice. Broadly speaking the film material is exposed once to the image of the object and separately with the raster with different portions of the film exposed in different sequence. One will proceed as follows. One half of film is exposed to the image of the object 3 for example of a person in front view. Concurrently and next to that particular film portion that is exposed to the image of the person the slide is in contact position with a film portion. Next the film is shifted so that that portion which was just exposed to the raster of the slide will be exposed to another image of object 3 such as person having changed position. That exposure step involves the film portion previously juxtaposed to the slide. The other portion of the film namely that one onto which was projected the image of the person in the first photographing step, now receives a superimposed raster of slide 11.

The invention has been described with reference to a photographic camera with a film being exposed to whatever illumination and radiation is provided for. However the principal employed is not tied to the photographic process as such. Rather, videotaping can be employed too, requiring so to speak an optical electromagnetic conversion step to be interposed. An example for videotaping is particularly envisioned if large areas are to be processed in this fashion. The video camera is preferably moved under observation of a constant space from the area to be measured and there along. A bundle of focused light such as a laser beam is always directed to the surface to be videotaped, possibly at an angle of 45 degrees. The laser is moved concurrently to the camera. The measuring raster is projected inside the video camera onto the same surface which provides for the optical-electrical conversion. A particular example for this kind of measuring method is the measurement of the internal contour of furnaces. Here the video camera is turned around the vertical axis of the furnace and axially shifted following each complete revolution to convert the entire interior of the furnace.

The invention is not limited to the embodiments described above but all changes and modifications thereof, not constituting departures from the spirit and scope of the invention, are intended to be included.

I claim:

1. Apparatus for ascertaining size, dimensional and topographic measurements of an object such as a person by means of photography whereby a measuring raster is to be superimposed on an image in a camera, the improvement comprising means (a) positioned inside the camera for projecting a slide raster inside the camera onto a photographic film therein; and means (b) disposed outside of the camera for projecting a horizontal line raster from outside of the camera onto said object.

2. Apparatus as in claim 1 the means (a) including a projector for a slide inside said camera and being attached to a housing wall thereof, there being a nearly 45 degrees inclined semi-transparent mirror for directing the slide projection into an optical imaging path and onto the photographic film of that imaging path.

3. Apparatus as in claim 1 the means (a) including a projector disposed at an angle for projecting a slide without interpositioning of a mirror directly onto the film.

4. Apparatus as in claim 1 and including a video camera instead of photographic camera.

5. Apparatus for acquiring the dimension of an object e.g. a person and including a photographic camera, a flash projector disposed for projecting a flash image of a horizontal line raster upon said object and at an oblique angle; the improvement comprising:

means inside said camera for superimposing a two-dimensional measuring raster upon the image through projection upon an image produced by the camera of the object.

6. Apparatus as in claim 5, wherein said means for superimposing is a means for projecting that includes a slidable raster plate inside the camera adjacent to the imaging plane.

7. Apparatus as in claim 5 the means inside the camera including a slide projector for projecting a slide carrying a measuring raster inside the camera.

* * * * *